United States Patent
Von Oepen

[11] Patent Number: 6,017,365
[45] Date of Patent: Jan. 25, 2000

[54] CORONARY STENT

[75] Inventor: Randolf Von Oepen, Hirrlingen, Germany

[73] Assignee: Jomed Implantate GmbH, Rangendingen, Germany

[21] Appl. No.: 09/093,844

[22] Filed: May 20, 1998

[30] Foreign Application Priority Data

May 20, 1997 [DE] Germany ................. 297 08 879 U

[51] Int. Cl.⁷ .................. A61F 2/06; A61F 2/04
[52] U.S. Cl. ........................ 623/1; 623/12
[58] Field of Search .................. 623/1, 12; 606/194, 606/198

[56] References Cited

U.S. PATENT DOCUMENTS

| | | | |
|---|---|---|---|
| 5,102,417 | 4/1992 | Palmaz | 606/195 |
| 5,383,892 | 1/1995 | Cardon et al. | 606/198 |
| 5,593,442 | 1/1997 | Klein | 623/12 |
| 5,697,971 | 12/1997 | Fischell et al. | 623/1 |
| 5,716,393 | 2/1998 | Lindenberg et al. | 623/1 |
| 5,733,303 | 3/1998 | Israel et al. | 606/198 |
| 5,827,321 | 10/1998 | Roubin et al. | 606/195 |
| 5,843,120 | 12/1998 | Israel et al. | 606/198 |
| 5,913,895 | 6/1999 | Burpee et al. | 623/1 |
| 5,938,697 | 8/1999 | Killion et al. | 623/1 |

FOREIGN PATENT DOCUMENTS

| | | |
|---|---|---|
| 19521581 | 12/1996 | Germany . |
| 29615969 | 12/1996 | Germany . |
| 29702671 | 5/1997 | Germany . |
| 29708689 | 8/1997 | Germany . |
| 9732543 | 9/1997 | WIPO . |

*Primary Examiner*—Mickey Yu
*Assistant Examiner*—Alvin Stewart
*Attorney, Agent, or Firm*—Shinjyu Global IP Counselors, LLP

[57] ABSTRACT

A coronary stent having a tubular body is disclosed. The tubular body has a wall which has a web structure and a flexible tip at at least one of its front ends. The web structure has a plurality of neighboring cells that are defined by webs.

25 Claims, 4 Drawing Sheets

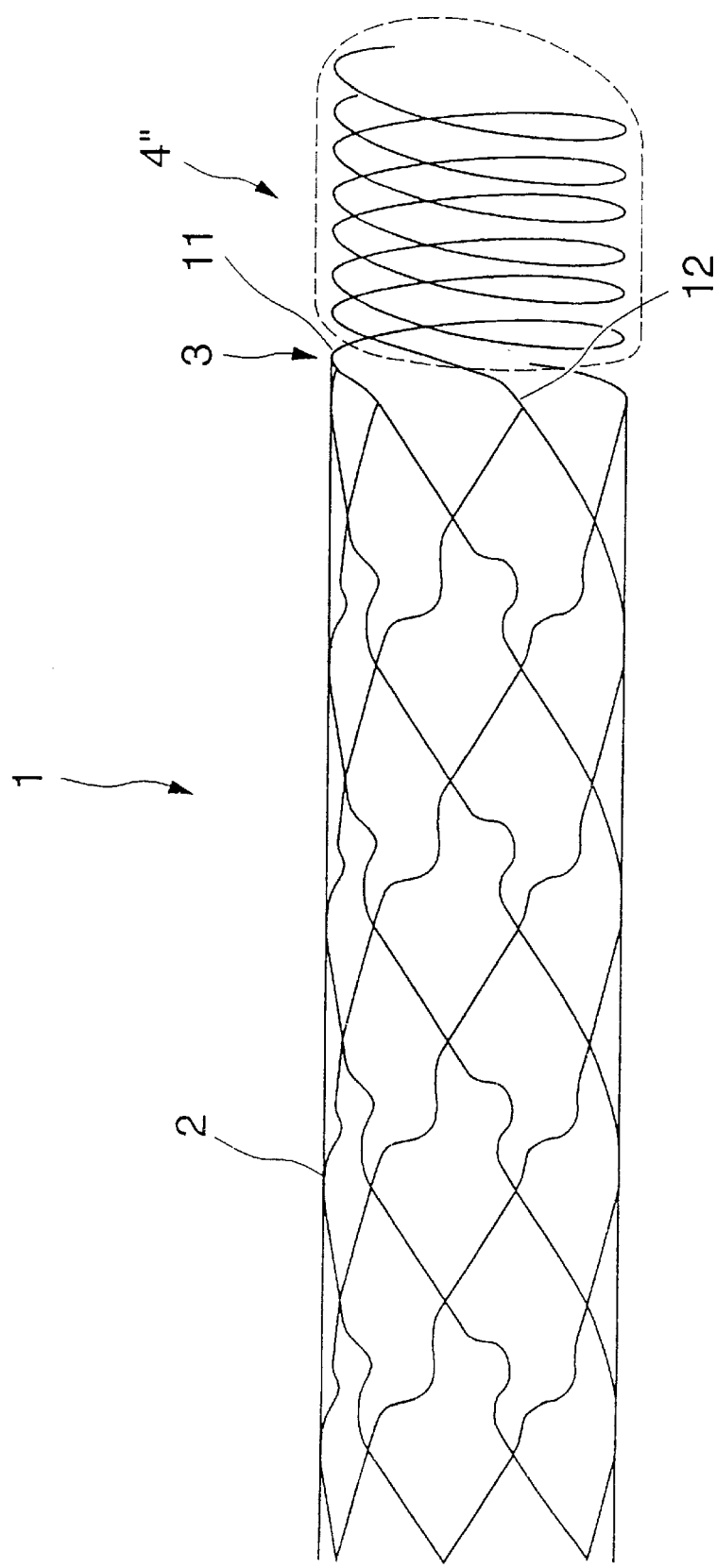

CORONARY STENT

FIELD OF THE INVENTION

The present invention relates to a coronary stent.

BACKGROUND OF THE INVENTION

Very different types of coronary stents are already known from the prior art. The stents form a vascular prosthesis made from a physically compatible material. The stent or stent prosthesis is used for expanding blood vessels or also other body orifices and for keeping said vessels in their expanded state. To this end, the stent is positioned in a patient's body in its non-expanded state and is then expanded by suitable means, for instance a balloon catheter. During expansion the individual web portions of the stent are deformed such that the stent permanently remains in its expanded form.

A stent of such a type is, for instance, shown in Utility Model 297 02 671.

When stents are constructed, the fundamental problem arises that these must have a sufficiently small diameter in their non-expanded state to be introducible into and positionable in a patient's body. The stents must be flexible along their longitudinal axis to some degree so as to be able to follow the shapes of, for instance, blood vessels. During expansion the stent must be expanded such that its outer diameter becomes considerably larger. Such an expansion is achieved by deforming the individual web portions in such a manner that no cracks, or the like, are formed.

SUMMARY OF THE INVENTION

It is the object of the present invention to provide a stent of the above-mentioned type which is of a simple structure, can easily be manufactured and safely used and is, nevertheless, extremely flexible and capable of applying and receiving sufficiently high radial forces.

This object is achieved according to the invention by a coronary stent having a tubular body. The tubular body has a wall which has a web structure and a flexible tip at at least one of its front ends. The web structure has a plurality of neighboring cells that are defined by webs.

The invention provides for an extremely flexible stent which can easily follow the windings of vessels when being inserted into a patient's body. Since the tip of the stent according to the invention is extremely flexible, the stent can follow the vessel windings very well and easily while being positioned, because it follows the guide wire of the balloon catheter, on which the stent is mounted during positioning, as if on a rail.

The inventive stent is thus characterized by a very high flexibility of its tip. During the positioning operation the stent is, so to speak, pulled by the tip through the vessel, as the tip can easily follow the vessel owing to its flexibility.

The flexible tip can be produced in various ways. In a preferred embodiment, a spiral is mounted at the end of the stent.

In a further, particularly preferred embodiment, connectors that have about the shape of a watch spring are formed at the end of the stent. A connector preferably engages only every second or third end of a web pattern that preferably extends in zig-zag fashion. Preferably, however, there should be at least three connectors so that the tip can very easily be coupled to the stent. At least one web pattern that extends in wound fashion is mounted on the connectors for forming the tip in a final manner. This subsequent web pattern (meander pattern) should preferably have short legs to avoid any inherent rigidity thereof. Such a design can preferably be achieved by increasing the number of zig-zag lines.

In a further, particularly preferred embodiment, a plurality of connectors and preferably short-legged meandering web patterns can alternately be mounted at the end of the stent.

Although a shape of the connectors in the form of a watch spring or a spiral represents a particularly preferred embodiment, other connectors that permit a flexible design of the tip are also possible in principle.

The inventive stent is characterized by several considerable advantages.

In the non-expanded state, the inventive assembly yields sufficient strength, but also high flexibility. The webs or web portions of the cells of the wall of the stent ensure that the stent can be expanded in an easy and reliable manner.

A zig-zag-shaped design of the folded webs of the first cells has turned out be very advantageous, so that these webs preferably form a band-like portion extending in circumferential direction. Such band-like portions increase the strength of the stent and also ensure its dimensional stability in the expanded state.

BRIEF DESCRIPTION OF THE DRAWINGS

The invention shall now be described with reference to three embodiments in conjunction with the drawing, in which:

FIG. 4 is an illustration, corresponding to FIGS. 2 and 3, of a third embodiment.

DETAILED DESCRIPTION OF THE INVENTION

Figure 1:
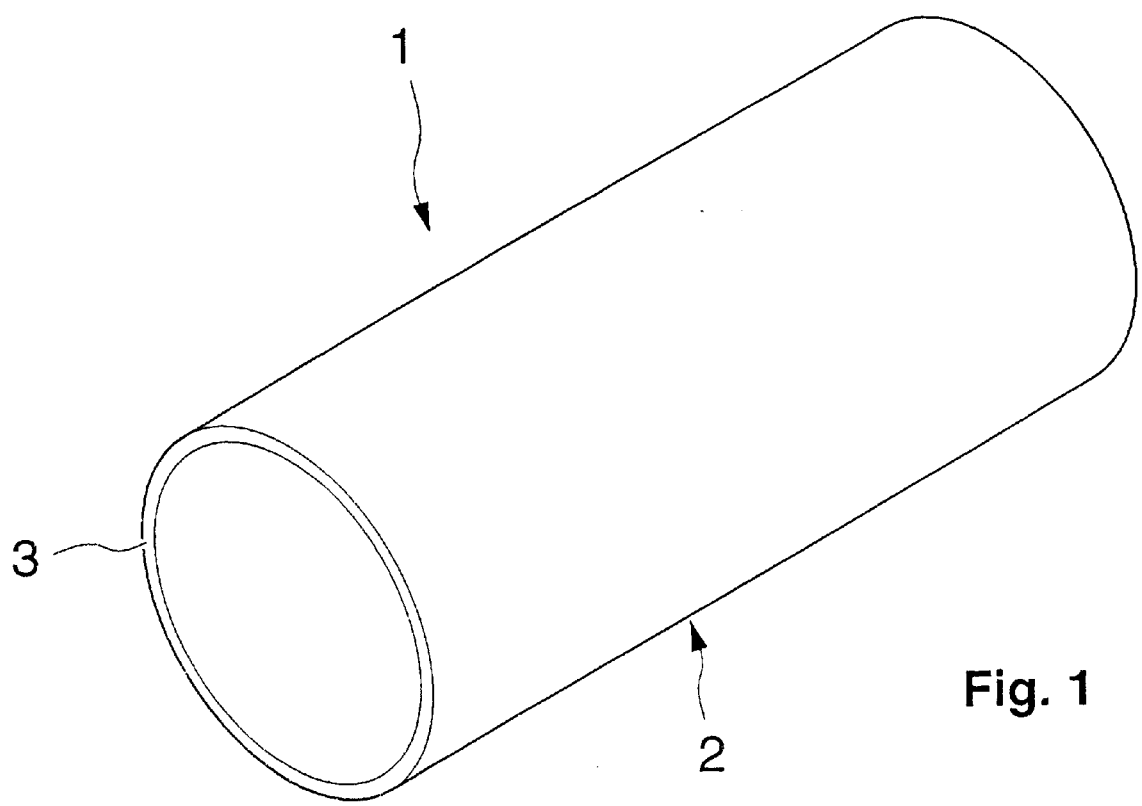
FIG. 1 is a schematically very simplified illustration of the basic structure of the stent according to the invention.

FIG. 1 shows the fundamental structure of an inventive stent 1 which comprises a flexible, tubular body 2 having a wall, of which the front end 3 is visible in FIG. 1.

Figure 2:
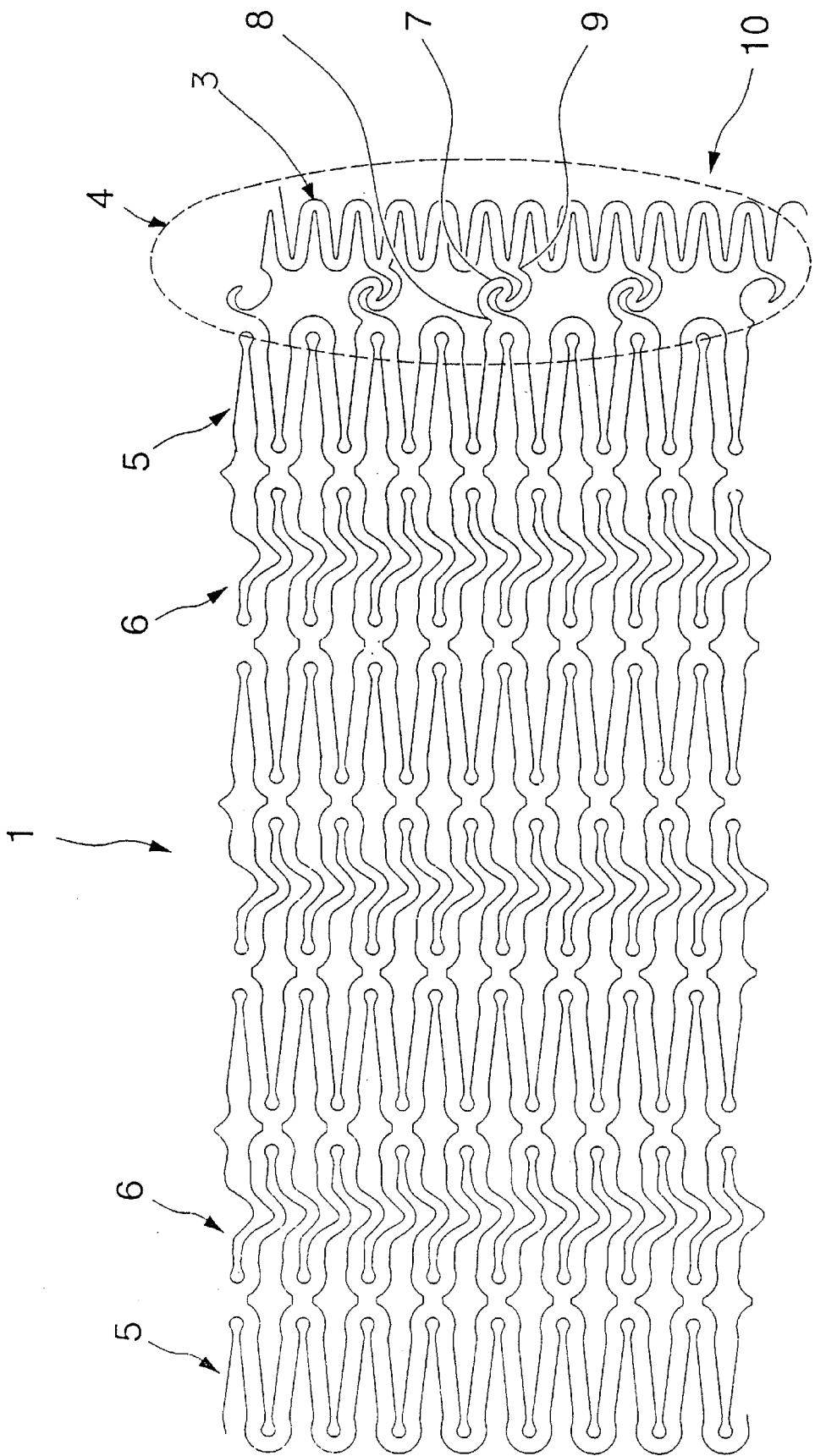
FIG. 2 is an illustration of a first embodiment of the web structure of the wall of the stent in the non-expanded state.

FIG. 2 shows a first embodiment of the inventive stent, wherein, for explaining the structure of the body 2, the wall thereof is illustrated in planar form according to the plane of drawing of FIG. 1.

As illustrated in FIG. 2, the stent 1 has a web structure which in the example alternately comprises web patterns 5 and 6, the web patterns 6 respectively interconnecting the web patterns 5. The web patterns 5 and 6 have webs which extend in zig-zag-like or meander-like fashion and define cells of the web structure.

A flexible tip 4 is arranged at the front end 3 of the inventive stent 1. In FIG. 2, this portion (flexible tip 4) of the stent 1 is encircled by a broken line.

In the embodiment illustrated in FIG. 2, the tip 4 has a plurality of preferably at least 3 connectors, of which one connector 7 is provided with a corresponding reference numeral and shown as a typical example. As illustrated in FIG. 2, the connector is s-shaped or spirally wound in a manner similar to the spring of a watch. At one of its free ends 8, the connector 7 is connected to the web patterns 5 provided at the front side. At the other free end 9 the connector 7 is arranged next to a further, preferably short-legged web pattern 10. The web pattern 10 is provided with shorter legs than the web patterns 5 and 6, respectively. It also extends in wound or zig-zag-shaped fashion and can thus also be referred to as a meander-like pattern.

The tip 4 in the above-described embodiment is extremely flexible, thereby permitting an insertion of the stent into a patient's body in a very reliable manner, as the flexible tip prevents the stent from getting entangled in the inner wall of the vessel and thus from injuring the wall.

Figure 3:
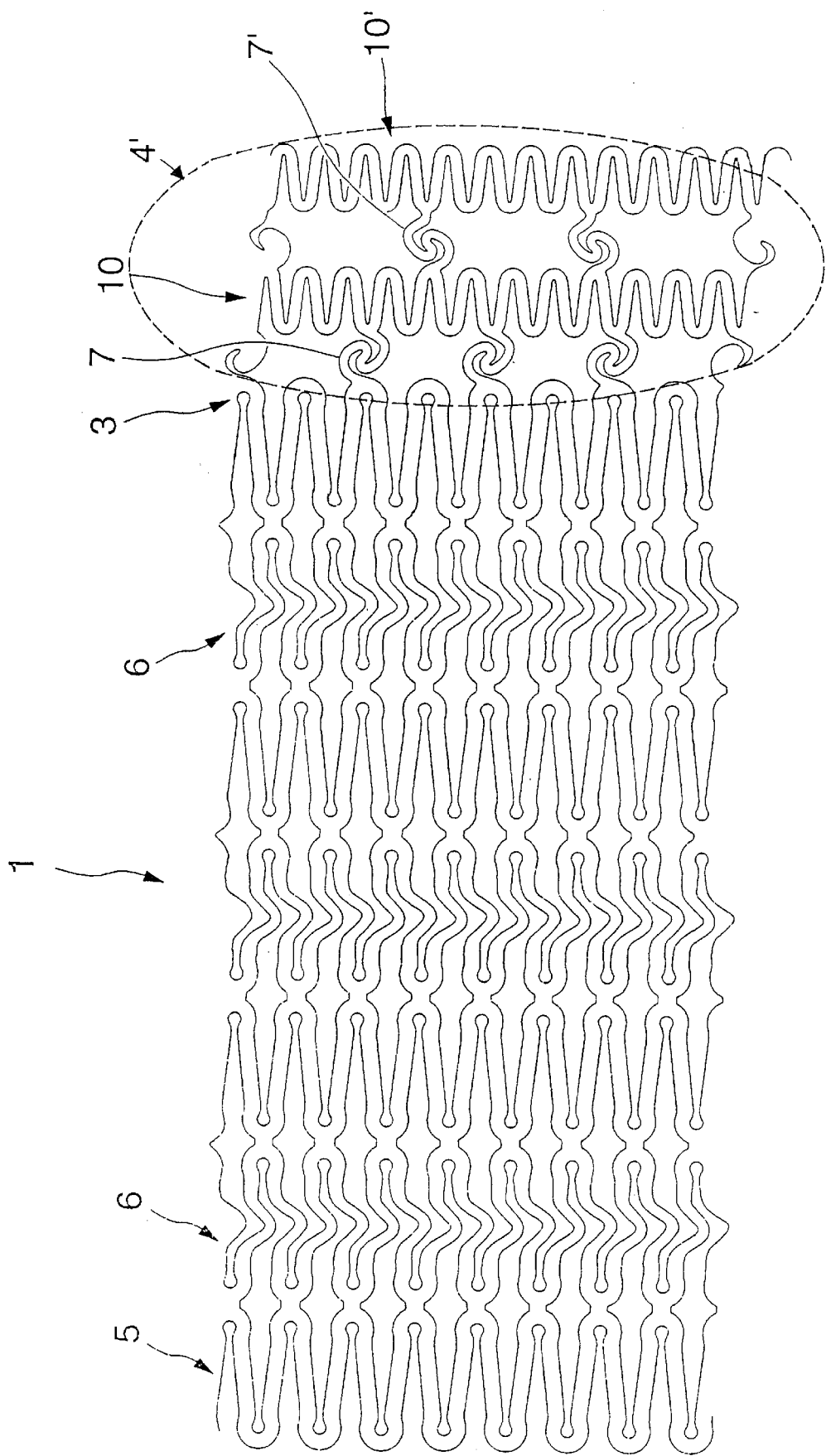
FIG. 3 is an illustration, corresponding to FIG. 2, of a second embodiment.

FIG. 3 illustrates a second embodiment of the inventive stent. All features that correspond to those shown in FIG. 2 are provided with identical reference numerals. The essential difference with respect to the embodiment according to FIG. 2 must be seen in the design of the flexible tip 4' which in the example comprises a further row of connectors 7' with a further web pattern 10' connected thereto, in addition to the plurality of connectors 4 and the web pattern 10 connected thereto. FIG. 3 illustrates that the connectors 7' are arranged relative to the connectors 7 such that they are bent by 180° and that the web pattern 10' is disposed such that it is phase-shifted with respect to the web pattern 10. Apart from that, however, reference can be made to the illustration in FIG. 2. Tip 4' is also very flexible and thus permits a reliable insertion of the stent into a patient's body, as said stent can very easily follow the windings of the vessels, even in cases where the web structure of the wall 2 is relatively rigid.

FIG. 4 is a schematically very simplified illustration showing a third embodiment. The stent 1 of this embodiment is provided at one of its front ends 3 with a flexible tip 4" which is formed as a spiral. The spiral 4" is connected to the web structure of the body 2 at two ends 11 and 12. The connection is preferably of an integral type which can also be used in the embodiments shown in FIGS. 2 and 3.

What is claimed is:

1. A coronary stent comprising
   a tubular body having a first end and a second end in which said tubular body is formed of a web structure, said web structure comprising a plurality of first main web patterns extending in a circumferential direction and a plurality of second main web patterns extending in a circumferential direction, said second main web patterns being different than said first main web patterns and being alternatingly coupled between adjacent pairs of said first main web patterns to form a plurality of neighboring cells, said first and second main web patterns having axial lengths; and
   a flexible tip having a first short-legged web pattern with an axial length, said first short-legged web pattern being coupled to at least one of said ends of said tubular body by a row of first connectors, said flexible tip further comprising a second short-legged web pattern with an axial length and at least one further row of second connectors, said second connectors being coupled between said first short-legged web pattern and said second short-legged web pattern, said axial lengths of said first and second short-legged web patterns being shorter in an axial direction than said axial lengths of said first and second main web patterns.

2. A coronary stent according to claim 1, wherein said first connectors are wound in s-shaped fashion.

3. A coronary stent according to claim 1, wherein said second connectors are wound in s-shaped fashion.

4. A coronary stent according to claim 2, wherein said second connectors are wound in s-shaped fashion.

5. A coronary stent according to claim 4, wherein said first connectors are wound in an opposite direction from said second connectors.

6. A coronary stent according to claim 1, wherein said first and second connectors are formed as spring elements of high elasticity.

7. A coronary stent according to claim 1, wherein said first and second main web patterns are zig-zag shaped band portions.

8. A coronary stent according to claim 7, wherein said first and second short-legged web patterns are zig-zag shaped band portions.

9. A coronary stent according to claim 7, wherein said first main web pattern is phase-shifted from said second main web pattern.

10. A coronary stent according to claim 7, wherein said first and second connectors are not axially aligned with each other.

11. A coronary stent according to claim 7, wherein said first main web pattern is different from said second main web pattern.

12. A coronary stent according to claim 9, wherein said first connectors are wound in s-shaped fashion.

13. A coronary stent according to claim 9, wherein said second connectors are wound in s-shaped fashion.

14. A coronary stent according to claim 12, wherein said second connectors are wound in s-shaped fashion.

15. A coronary stent according to claim 14, wherein said first connectors are wound in an opposite direction from said second connectors.

16. A coronary stent according to claim 14, wherein said first and second connectors are not axially aligned with each other.

17. A coronary stent according to claim 14, wherein said first main web pattern is different from said second main web pattern.

18. A coronary stent according to claim 1, wherein said first and second short-legged web patterns are zig-zag shaped band portions.

19. A coronary stent according to claim 18, wherein said first short-legged web pattern is phase shifted from said second short-legged web pattern.

20. A coronary stent according to claim 19, wherein said first connectors are wound in s-shaped fashion.

21. A coronary stent according to claim 20, wherein said second connectors are wound in s-shaped fashion.

22. A coronary stent according to claim 21, wherein said first connectors are wound in an opposite direction from said second connectors.

23. A coronary stent according to claim 21, wherein said first and second connectors are not axially aligned with each other.

24. A coronary stent according to claim 23, wherein said first main web pattern is different from said second main web pattern.

25. A coronary stent according to claim 23, wherein said first and second main web patterns are zig-zag shaped band portions.

* * * * *